(12) United States Patent
Shiraishi et al.

(10) Patent No.: US 7,763,756 B2
(45) Date of Patent: Jul. 27, 2010

(54) METHOD FOR COLLECTING OBJECT MATERIAL FROM SOLUTION

(75) Inventors: Shigenori Shiraishi, Ichihara (JP); Shigeru Goto, Chiba (JP); Masaaki Katao, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 497 days.

(21) Appl. No.: 10/572,877

(22) PCT Filed: Sep. 16, 2004

(86) PCT No.: PCT/JP2004/013991

§ 371 (c)(1),
(2), (4) Date: Mar. 22, 2006

(87) PCT Pub. No.: WO2005/030359

PCT Pub. Date: Apr. 7, 2005

(65) Prior Publication Data

US 2007/0123721 A1 May 31, 2007

(30) Foreign Application Priority Data

Sep. 25, 2003 (JP) ............................. 2003-333159
Mar. 10, 2004 (JP) ............................. 2004-067149

(51) Int. Cl.
*C07C 407/00* (2006.01)
(52) U.S. Cl. ..................... 568/576; 549/529
(58) Field of Classification Search ................. 549/529; 568/576

See application file for complete search history.

(56) References Cited

U.S. PATENT DOCUMENTS 4,036,890 A * 7/1977 Ester et al. .................. 568/569
6,063,281 A * 5/2000 Bonkhoff et al. ............ 210/638

FOREIGN PATENT DOCUMENTS

| JP | 59-169505 A | 9/1984 |
| JP | 4-225802 A | 8/1992 |
| JP | 2003-183248 A | 7/2003 |
| JP | 2003-261552 A | 9/2003 |

OTHER PUBLICATIONS

Nekrasov et al., Chemistry and Technology of Fuels and Oils, 1980, 16(2), 99-103.*
USEPA Contract Laboratory Program Statement of work for Organics Analysis, May 1999, Section 10.1.3.1.3, D-34/PEST.*

* cited by examiner

*Primary Examiner*—Janet L Andres
*Assistant Examiner*—David E Gallis
(74) *Attorney, Agent, or Firm*—Sughrue Mion, PLLC

(57) ABSTRACT

A method for collecting an object material from a solution, which comprises the following steps:
 a step of adding a second solvent to a solution composed of an object material to be collected and a first solvent, then mixing therewith to form an emulsion containing the object material in a state under which the emulsion is not uniformly dissolved in the second solvent, in the second solvent; and
 a step of separating thus obtained emulsion from the solution.

9 Claims, No Drawings

METHOD FOR COLLECTING OBJECT MATERIAL FROM SOLUTION

TECHNICAL FIELD

The present invention relates to a method for collecting an object material from a solution.

BACKGROUND ART

As methods for collecting an object material from a solution, a distillation method utilizing difference in boiling points among chemical compounds or crystallization method utilizing the difference in solubilities among them are used.

However, the object material may be deteriorated in heating because, in these methods, an object component or other components from a mixed solution must be selectively evaporated or precipitated or crystallized. Further, large energy often becomes necessary for cooling or heating, therefore, these are unsatisfactory in the viewpoint of energy saving.

In addition, as another method, a liquid membrane separation method is known (see "Chemical Engineering Handbook, 6$^{th}$ revised Edition, pages 660). However, the separation method is a method utilizing difference in rates of passing through the liquid membrane between an object component and other components in a raw liquid material, for example, since a publicly known separation technique (see JP05239469 A) utilizing an emulsified membrane is a non-equilibrium separation in which an emulsion formed once is dispersed in another phase to form a multiple=emulsion, then extraction and reverse extraction are simultaneously carried out, it cannot be satisfied due to requirements of complex steps and operation conditions.

DISCLOSURE OF THE INVENTION

An object of the present invention is to provide a method for collecting an object material from a solution containing the object material, which can collect the object material in which heating of the solution required in distillation is not essential thereby collecting the object material unstable against heat without deterioration and which is also excellent from the viewpoint of energy saving.

The present invention relates to a method for collecting an object material from a solution, which comprises the following steps:

a step of adding a second solvent to a solution composed of an object material to be collected and a first solvent, then mixing therewith to form an emulsion containing the object material in the second solvent in a state of which the emulsion is not uniformly dissolved in the second solvent; and a step of separating thus obtained emulsion from the solution.

BEST MODE FOR CARRYING OUT THE INVENTION

In the present invention, as an object material to be collected, a material having at least two parts having different lyophilic properties individually, for example, a chemical compound having a lipophilic part and hydrophilic part, can be listed. Generally, the lipophilic part is a part mainly composed of a hydrocarbon and the hydrophilic part is a part at which mainly oxygen and hydrogen are bonded. Specific examples of the object material include organic hydroperoxide such as alkylbenzene hydroperoxides (e.g. ethylbenzene hydroperoxide, cumene hydroperoxide, isobutylbenzene hydroperoxide, t-butylbenzene hydroperoxide), and alkyl hydroperoxides (e.g. t-butyl hydroperoxide). The organic hydroperoxide can be obtained byoxidizing an organic compound, and particularly, alkylbenzene hydroperoxides obtained by oxidizing alkylbenzenes are preferably suitable.

The first solvent may be a solvent which dissolves the object material and does not uniformly mix with the second solvent, preferably, organic solvents are used.

Examples of the organic solvent include ketones (e.g. methylethylketone, methylisobutylketone), ethers (e.g. ethylether, n-butylether), carboxylic esters (e.g. ethyl acetate), aliphatic hydrocarbons (e.g. n-hexane, n-heptane, n-octane, n-decane) and aromatic hydrocarbons (e.g. benzene, toluene, xylene, ethylbenzene, cumene, t-butylbenzene), and among these, aliphatic or aromatic hydrocarbons are preferred.

Herein, a solution means a liquid in which the object material is substantially uniformly dissolved in the first solvent.

In the present invention, collection of the object material means collecting at least a part of the object material.

The second solvent is a one which does not uniformly dissolve the object material and does not uniformly mix with the first solvent, and which forms an emulsion by mixing with the solution containing the above-mentioned object material and exhibits lyophilic properties with a group of the object material, and, for example, water is preferable.

According to the present invention, it was found that the rate of the object material to the first solvent in the formed emulsion became extremely higher than that of the object material to the first solvent in the solution, namely, the object material in the first solvent could be effectively concentrated.

In a step of forming the emulsion, a mixed liquor of the solution with the second solvent is separated into a solution phase composed of the first solvent and the object material which was not collected and a phase of the emulsion.

As a preferable mixing method for forming the emulsion, for example, a method using ultrasonic irradiation or mechanical agitation, can be listed. Namely, as mentioned above, the emulsion is formed by irradiating ultrasonic to the mixed liquor of the solution with the second solvent and/or mechanically agitating the mixed liquor thereof. It is separated into two phases by being allowed to stand still after forming the emulsion.

For carrying out a step for separation of the emulsion obtained in the emulsion-forming step from the solution, the solution phase composed of the first solvent and the object material which has not been collected and the phase of the emulsion may be separated at an interface of the both phases.

In the present invention, there may be set up a step of collecting of the object material from the emulsion after the separation step.

As a collecting method, a method of subjecting the emulsion to centrifugal separation, a method of collecting through extraction of the object material from the emulsion using an extractant or the like, can be listed. In a case of extraction, it is preferable to use steps of carrying out extraction with an extractant of which a boiling point of the extractant is lower than both of the object material and the second solvent, further then subjecting an extracted mixture thus obtained to distillation to separate and collect the object material.

The method of the present invention can be preferably applied to at least a part of an concentration step in a process for producing propylene oxide containing an oxidation step of obtaining an organic hydroperoxide by oxidation of an organic compound, a concentration step of concentrating the organic hydroperoxide and an epoxidation step of obtaining propylene oxide by reacting the organic hydroperoxide with propylene (for example, JP2003-327576 A). As a preferable specific example of this case, there can be illustrated a case that the object material to be collected is cumene hydroperoxide (CMHP), the first solvent is an organic solvent containing mainly cumene and the second solvent is a solvent containing mainly water.

EXAMPLE

Example 1

An organic solvent containing mainly cumene as the first solvent containing 24.7% by weight of cumene hydroperoxide (CMHP) as an object material, was contacted with water as the second solvent under ordinary temperature and pressure and mixed by ultrasonic irradiation until an aqueous phase became clouded. After thus obtained mixed liquid was allowed to stand until the liquid was separated into an oil phase and an aqueous phase containing a clouded emulsion, the aqueous phase containing the clouded emulsion was isolated. This clouded aqueous phase was subjected to centrifugal separation for 1 hour to obtain two liquid phases of a transparent aqueous phase and an oil phase. After the oil phase was separated off, when a CMHP concentration was measured by an iodometric titration, the concentration was 66.3% by weight. It is found that CMHP existed at the rate of 24.7% by weight in the solution was concentrated to 66.3% by weight and was selectively collected.

Example 2

After an organic solvent containing mainly cumene as the first solvent containing 24.6% by weight of cumene hydroperoxide (CMHP) as an object material and a solvent containing mainly water were mechanically agitated under 65° C. about 1200 kPa, the resultant was separated into an oil phase and a clouded emulsion utilizing a difference between specific gravities thereof.

This clouded aqueous phase was subjected to centrifugal for 1 hour to obtain to two liquid phases of a transparent aqueous phase and an oil phase. After the oil phase was separated off, when a CMHP concentration was measured by an iodine titration method, the concentration was 69.0% by weight. It is found that CMHP existed at the rate of 24.6% by weight in the solution was concentrated to 69.0% by weight and was selectively collected, by the above-mentioned operation.

INDUSTRIAL APPLICABILITY

According to the present invention, there can be provided a method for collecting an object material from a solution containing the object material, which can collecting the object material in which heating of the solution required in distillation is not essential thereby collecting the object material unstable against heat without deterioration and which is also excellent from the viewpoint of energy saving.

The invention claimed is:

1. A method for collecting an object material from a solution, which comprises the following steps:
    a step of adding a second solvent to a solution composed of an object material to be collected and a first solvent, then mixing therewith to form an emulsion containing the object material in the second solvent, in a state of not being uniformly dissolved in the second solvent; and
    a step of separating thus obtained emulsion from the solution,
    wherein the first solvent is an organic solvent, the second solvent is water, and the object material is an organic hydroperoxide.

2. The method according to claim 1, wherein the emulsion is formed using ultrasonic or mechanical agitation.

3. The method according to claim 1, further comprises a step of collecting the object material from the emulsion obtained in the separating step after the separating step.

4. The method according to claim 3, wherein the step of collecting the object material from the emulsion comprises centrifugal separation.

5. The method according to claim 3, wherein the step of collecting the object material from the emulsion comprises extracting the object material from the emulsion using an extractant.

6. The method according to claim 5, wherein the extractant is a one having a boiling point lower than that of any of the object material and the second solvent.

7. The method according to claim 6, further comprises a step of separating the object material by subjecting an extracted mixture obtained by extracting the object material from the emulsion using an extractant to distillation.

8. The method according to any one of claims 1 to 6, wherein the collecting method is at least a part of an concentration step in a process for producing propylene oxide comprising an oxidation step of obtaining an organic hydroperoxide by oxidation of an organic compound, a concentration step of concentrating the organic hydroperoxide and an epoxidation step of obtaining propylene oxide by reacting the organic hydroperoxide with propylene.

9. A process for producing propylene oxide, which comprises an oxidation step of obtaining an organic hydroperoxide by oxidation of an organic compound, a concentration step of concentrating the organic hydroperoxide and an epoxidation step of obtaining propylene oxide by reacting the organic hydroperoxide with propylene, wherein at least a part of the concentration step is any one of claims 1 to 6.

* * * * *